United States Patent
Reiderman et al.

(10) Patent No.: US 6,525,535 B2
(45) Date of Patent: Feb. 25, 2003

(54) NMR APPARATUS FOR OIL WELL LOGGING OF LARGE AND SMALL DIAMETER WELLS

(75) Inventors: Arcady Reiderman, Houston, TX (US); David R. Beard, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/997,451

(22) Filed: Nov. 30, 2001

(65) Prior Publication Data

US 2002/0140424 A1 Oct. 3, 2002

Related U.S. Application Data

(63) Continuation-in-part of application No. 09/677,359, filed on Oct. 2, 2000, now Pat. No. 6,348,792.

(51) Int. Cl.$^7$ .................................................. G01V 3/00
(52) U.S. Cl. ......................................... 324/303; 324/300
(58) Field of Search ................................ 324/303, 300, 324/307, 309, 338, 314, 322

(56) References Cited

U.S. PATENT DOCUMENTS

| | | | |
|---|---|---|---|
| 4,350,955 A | 9/1982 | Jackson et al. ............. 324/303 |
| 4,717,877 A | 1/1988 | Taicher et al. .............. 324/303 |
| 5,055,787 A | 10/1991 | Kleinberg et al. .......... 324/303 |
| 5,488,342 A | 1/1996 | Hanley ........................ 335/306 |
| 5,646,528 A | 7/1997 | Hanley ........................ 324/303 |
| 6,023,164 A | 2/2000 | Prammer .................... 324/303 |
| 6,445,180 B1 * | 9/2002 | Reiderman et al. ......... 324/303 |

* cited by examiner

*Primary Examiner*—Edward Lefkowitz
*Assistant Examiner*—Brij B. Shrivastav
(74) *Attorney, Agent, or Firm*—Madan, Mossman & Sriram, P.C.

(57) ABSTRACT

The invention is a method and apparatus for performing NMR measurements in MWD effective for large and small boreholes. The invention uses a magnet assembly to produce a generally oval static magnetic field. The invention also employs an antenna assembly comprised of a primary and secondary antenna to deliver a sequence of RF magnetic pulses. For small holes, the antenna assembly operates to substantially match the iso-lines of the static magnetic field within the rock formation during a transmission pulse. For large holes, the invention works in a side-looking mode and the antenna assembly operates both to match the iso-lines of the static magnetic field within the rock formation and to diminish the magnetic field within the borehole during a transmission pulse. The secondary antenna can also be used as a receiver of spin echo signals, or optionally, to make adjustments to the received signal.

16 Claims, 3 Drawing Sheets

NMR APPARATUS FOR OIL WELL LOGGING OF LARGE AND SMALL DIAMETER WELLS

This application is a continuation-in-part of U.S. patent application Ser. No. 09/677,359, filing date Oct. 2, 2000 now U.S. Pat. No. 6,348,792 (the "Relderman '792") and is also related to U.S. patent applications Ser. No. 09/605,265, now U.S. Pat. No. 6,445,180 (the "Reiderman '180"), the contents of which are fully incorporated herein by reference.

BACKGROUND OF THE INVENTION

1. Field of the Invention

The invention is in the field of Nuclear Magnetic Resonance testing equipment. In particular the invention is an apparatus for NMR testing to be used for determining with greater accuracy the values of formation properties in borehole drilling.

2. Description of the Related Art

A variety of techniques have been used in connection with wellbore drilling to determine the presence of and to estimate quantities of hydrocarbons (oil and gas) in earth formations surrounding the wellbore. These methods are designed to determine formation parameters including, among other things, porosity, fluid content, and permeability of the rock formation. Typically, the tools designed to provide the desired information are used to log the wellbore. Much of the logging is done after the wellbore has been drilled. Removing the drilling apparatus in order to log the wellbore can prove costly in terms of time and money. More recently, wellbores have been logged simultaneously with drilling of the wellbores, which is referred to as measurement-while-drilling ("MWDV") or logging-while-drilling ("LWD"). Measurements have also been made when tripping a drillstring out of a wellbore. This is called measurement-while-tripping ("MWT").

One recently evolving technique involves utilizing Nuclear Magnetic Resonance (NMR) logging tools and methods for determining, among other things, porosity, hydrocarbon saturation, and permeability of the rock formations. The NMR logging tools are utilized to excite the nuclei of the fluids in the geological formations in the vicinity of the wellbore so that certain parameters such as spin density, longitudinal relaxation time (generally referred to in the art as "$T_1$"), and transverse relaxation time (generally referred to as "$T_2$") of the geological formations can be estimated. From such measurements, porosity, permeability, and hydrocarbon saturation are determined, which provides valuable information about the make-up of the geological formations and the amount of extractable hydrocarbons.

NMR well logging instrument typically include a permanent magnet to induce a static magnetic field in the earth formations and a transmitting antenna, positioned near the magnet and shaped so that a pulse of radio frequency (RF) power conducted through the antenna induces an RF magnetic field in the earth formation. The RF magnetic field is generally orthogonal to the static magnetic field. After an RF pulse, voltages are induced in a receiving antenna by precessional rotation of nuclear spin axes of hydrogen or other nuclei about the static magnetic field. The precessional rotation occurs in an excitation region where the static magnetic field strength corresponds to the frequency of RF magnetic field. A sequence of RF pulses can be designed to manipulate the nuclear magnetization, so that different aspects of the NMR properties of the formation can be obtained.

For NMR well logging the most common sequence is the CPMG sequence that comprises one excitation pulse and a plurality of refocusing pulses. It is the intent of NMR methods that the region of interest, as defined by the placement of the magnetically induced fields, lies totally within the rock formation. These field lines can, however, lie within the borehole, thus producing erroneous signals. Due to differing geometries of boreholes, different methods of NMR logging have been devised. For a small axially symmetric borehole in which the probing device is centrally located, it is possible to obtain information from an axially: symmetric region within the rock formation.

U.S. Pat. No. 4,350,955 to Jackson et al. discloses a pair of permanent magnets arranged axially within the borehole so their fields oppose, producing a region near the plane perpendicular to the axis, midway between the sources, where the radial component of the field goes through a maximum. Near the maximum, the field is homogeneous over a toroidal zone centered on the borehole. With the Jackson arrangement, the axial extent of the region of examination is quite limited. As a result of this, the device can only be operated at relatively low logging speeds. Otherwise, because of the tool motion during logging, the magnitude of the static field changes significantly within a fixed region of the formation with an accompanying degradation of NMR signals.

A "side-looking" NMR tool is sensitive to NMR excitation on one side of the tool and less sensitive to NMR excitation on the other side. The more sensitive side of the tool is typically pressed against the sidewall of a borehole adjacent a formation, thereby providing minimum separation between the NMR tool's RF field generating assembly and the formation volume of NMR investigation. The less sensitive side of the tool is thus exposed to the borehole. This operational NMR technique is most effective when the borehole diameter is much greater!than the diameter of the NMR tool.

Typically, side-looking NMR tools set up static and RF magnetic field distributions in a particular relationship to achieve maximum NMR sensitivity on one side of the NMR tool. These conventional side looking NMR techniques are well known in the art, as taught in the following patents: U.S. Pat. No. 4,717,877, Taicher et al., entitled Nuclear Magnetic Resonance Sensing Apparatus and Techniques, U.S. Pat. No. 5,055,787, Kleinberg et al., entitled Borehole: Measurements Of NMR Characteristics Of Earth Formation; U.S. Pat. No. 5,488,342, Hanley, entitled Magnet Assembly For NMR; U.S. Pat. No. 5,646,528, Hanley, entitled Magnet Assembly; and U.S. Pat. No. 6,0213,164, Prammer et al. entitled Eccentric NMR Well Logging Apparatus And Method.

The Kleinberg '787 patent teaches a side-looking NMR tool which generates a static magnetic field which results in a sensitive volume on only the front side of the tool. The sensitive region in front of this tool generates a field having a substantially zero gradient, while the region behind this tool has a relatively large gradient field. Consequently, the volume of the sensitive NMR region in front of the tool is much larger and contributes more significantly to the composite NMR signal, than does the NMR region behind the tool. The '787 patent technique, however, is only practical when the sensitive volume in front of the tool is very close to the tool. This condition therefore limits the available depth of NMR investigation. The '787 tool design also requires a substantially zero gradient in the sensitive volume. Such a zero gradient is not always desirable, however, in NMR well logging, as a number of associated NMR techniques depend upon having a finite, known gradient within the NMR sensitive volume.

The Hanley '342 patent teaches a NMR tool technique which provides a homogeneous region localized in front of the tool. The '342 tool design overcomes the disadvantageous requirement of the sensitive volume being undesirably close to the NMR tool. However, it suffers because the sensitive volume is not elongated along the longitudinal axis of the NMR tool or bore hole axis, causing unacceptable errors due to motional effects.

Hanley '528 discloses another variation of the Jackson device in which a shield of electrically conductive material is positioned adjacent to and laterally offset from the set of electrical coils whereby the magnetic field generated by the RF antenna is asymmetrically offset from the axis of the magnets. The region of uniform static field remains a toroid, as in the Jackson device. The Hanley '528 device may be operated eccentrically within a large borehole with a reduction in the borehole signal. Both of the Hanley devices suffer from the drawback that the axial extent of the region of examination is small, so that they cannot be operated at high logging speeds.

There are several devices in which the problem of limited axial extent of the basic Jackson configuration of permanent magnets is addressed. U.S. Pat. No. 4,717,877 to Taicher et al teaches the use of elongated cylindrical permanent magnets in which the poles are on opposite curved faces of the magnet. The static field from such a magnet is like that of a dipole centered on the geometric axis of the elongated magnets and provides a region of examination that is elongated parallel to the borehole axis. The RF coil in the Taicher device is also a dipole antenna with its center coincident with the geometric axis of the magnet, thereby providing orthogonality of the static and magnetic field over a full 360° azimuth around the borehole.

U.S. Pat. No. 6,023,164 to Prammer discloses a variation of the Taicher patent in which the tool is operated eccentrically within the borehole. In the Prammer device, NMR logging probe is provided with a sleeve having a semi-circular RF shield covering one of the poles of the magnet. The shield blocks signals from one side of the probe. The probe is provided with elements that press the uncovered side of the probe to the sidewall of the borehole so that signals received by the uncovered side arise primarily from the formation.

For both the Prammer '164 and the Hanley '528 devices, in order to get the best attenuation in the field behind the probe while maintaining sensitivity in front of the probe, the shield should be positioned as far away from the front region as possible. The effectiveness of the shield is limited by the diameter of the tool. In the absence of a shield, the Prammer '164 and Hanley '528 tools have a circular sensitive region, so that use of either device in an eccentric manner would result in a large signal from the borehole fluid.

The passive RF shield is typically positioned as far as possible from the front region in order not to spoil NMR tool sensitivity in the desired region and as close as possible to the back region for maximum effectiveness. It can be seen therefore that the effectiveness of the passive shield will eventually be limited by the diameter of the tool. If we can not achieve sufficient attenuation with a shield inside the tool we will have to adopt one of the following undesirable options: use the large magnet to move the rear region further away; reduce the signal from the front region; or place a shield outside the tool. Thus, neither approach presents a practicable solution.

Reiderman '180 teaches a method of creating a RF field through use of a primary and secondary antenna system. The primary antenna, being the larger of the two, creates a volumetrically extended magnetic field, most of which extends into the rock formation, and some of which lies within the borehole. The secondary antenna acts synchronously with the primary antenna, but its current circulates in a direction opposite to the direction of the current in the primary antenna, causing a magnetic field that cancels the magnetic field of the primary antenna in the region inside the borehole, thereby significantly reducing contributions from the borehole to the sensed NMR signal.

Reiderman '792 introduces a configuration of a primary static magnet with a secondary shaping magnet. The shaping magnet is used to shape the static magnetic field to conform to the RF field over a larger azimuthal sector around the tool. A shield in the back part of the device reduces the RF field behind the tool. The static and RF dipoles are rotated 90° relative to prior art, so that the static dipole points to the side of the tool and the RF dipole to the front of the tool. With this arrangement, eddy currents in the shield are substantially increased, increasing its effectiveness.

A limitation of these particular applications is that the device has only a side-looking mode, which is useful for large boreholes. However, for small boreholes, it is advantageous to use a central mode which excites signals on all sides of the NMR tool. Logging of boreholes with different diameters would thus require the use of different tools and an associated increase in costs due to having a larger inventory of tools.

One way to avoid having a large number of different tools would be to design a NMR tool that generates a static field so that the resonant region behind the tool is so far away that it never encroaches into any reasonably expected borehole diameter. This, however, would either require stronger magnets than are currently being used, or a lowering of the tool operating frequency. Stronger magnets are undesirable because they increase the cost, weight and size of the instrument. Moreover, the stronger magnets may attach to the wellbore casing, making it difficult or impossible to pass the NMR tool through the casing to the borehole. Additionally, lowering the tool frequency is not desirable, because it lowers the signal-to-noise ratio for the NMR measurement.

There is a need for a device that can operate in both large and small boreholes. Such a device should preferably be not unduly heavy or have extraordinarily strong permanent magnets that might have difficulty going through a cased borehole. The present invention satisfies this need.

SUMMARY OF THE INVENTION

The invention is an NMR tool design adaptable for NMR oil testing in boreholes with both large and small radii. The invention comprises a magnetic assembly that produces a oval shaped magnetic field surrounding the NMR assembly. The invention also comprises an antenna assembly including a primary antenna and a secondary antenna. The magnetic fields of the two coils can be altered, depending on the direction of the currents within the coils, to either work additively or work against each other. The advantage of this configuration is that the shape of the sensitive region can be altered to fit logging conditions. The direction of the current in the secondary coil is responsible for the shape of the sensitive region. It may be used in either a booster mode or in a spoiler mode.

The booster mode is effective for use in small boreholes. In this mode the sensitive region due to the static field of the magnet assembly lies generally entirely within the rock formation. During the transmission portion of the pulse sequence, the magnetic field of the secondary coil shares the same orientation as that of the primary coil, with both fields being substantially parallel and combining to form a RF magnetic field that matches one of the iso-lines of the static magnetic field. During the receiving portion of the pulse sequence, both antennae receive the signals from the rock formation. The secondary coil operates during both the transmission and receiving portions of the pulse sequence.

In the spoiler mode, by intent, the secondary coil of the antenna assembly operates only during the transmission portion of the pulse sequence and can either operate or be inactive during the receiving portion of the pulse. The secondary coil creates a magnetic field which opposes and is anti-parallel to that of the primary coil and which ideally causes the magnetic field on the back side of the tool to vanish. This method creates a sensitive region which lies solely on the front side of the tool. The tool can thereby be use as a side-looking NMR device. During the receiving portion, the secondary antenna is turned off, with the advantage that, by its inactivity, it does not receive any erroneous signals that might still come from inside the borehole. Optionally, the secondary coil can be used to indicate any residual signal from inside the borehole, thereby deducing a necessary correction to the signal.

DESCRIPTION OF PREFERRED EMBODIMENT

Figure 1:
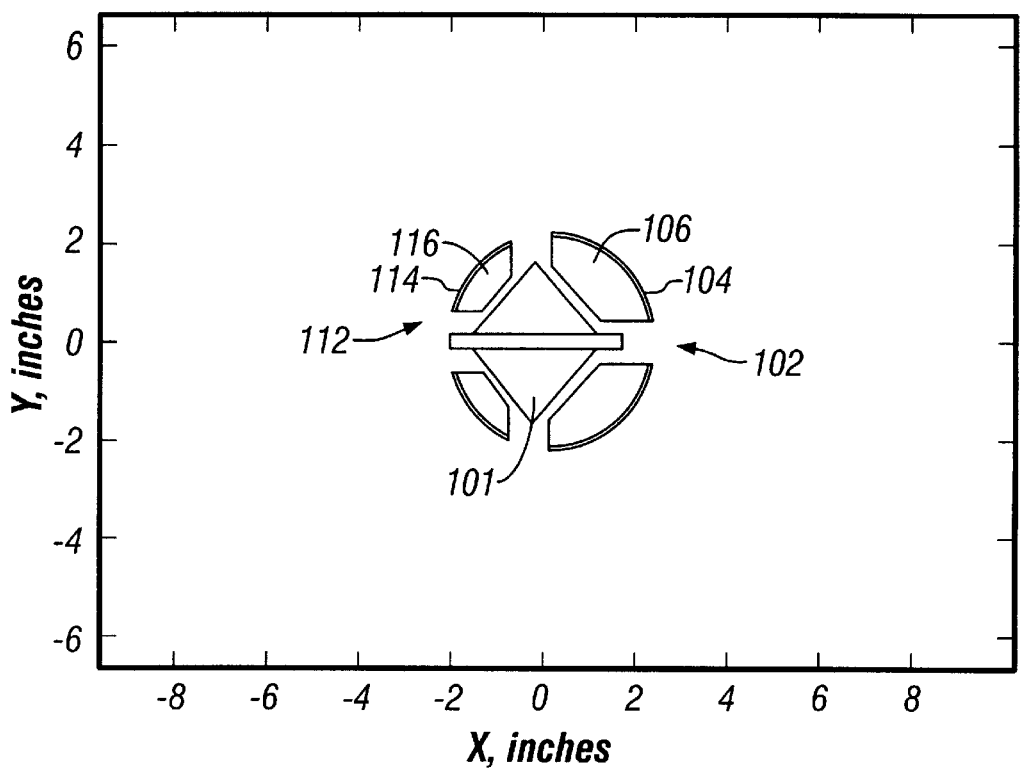
FIG. 1 shows a cross-sectional view of the NMR detection apparatus.

FIG. 1 shows a cross-sectional view of the preferred NMR logging tool which is to be perpendicular to the axis of the borehole. The logging tool is comprised of a magnetic assembly 101 generally centered on a permanent asymmetric magnet. The magnet, as shown in FIG. 1, is notable as containing only one axial line of symmetry, but the shape illustrated is only one of many possible shapes for the permanent magnetic as long as the magnet maintains the axial line of symmetry. The permanent magnet 101 induces a static magnetic field in a required distribution throughout the borehole, Adjacent to one side of magnet 101 is a primary antenna 102, and on the other side is a secondary antenna 112 The primary antenna is situated in the direction herein referred to as the front side, while the secondary antenna is situated on the back side. It is the intention that the front side is placed up against the borehole wall, or generates magnetic fields always extending into the rock formation. Each antenna comprises an antenna winding and a soft magnetic core. For the primary antenna 102, the antenna winding is labeled 104 and the soft magnetic core is labeled 106. For the secondary antenna 112, the antenna winding is labeled 114 and the soft magnetic core is labeled 116.

The primary antenna affects a larger volume than the secondary antenna, and so delivers the primary RF pulse used in the process. The secondary antenna is employed to alter the shape of the RF magnetic fields behind the permanent magnet. The secondary antenna can work in either a spoiler mode or in a booster mode, determined according to the direction of current flow through the antenna. In the mode in which the secondary antenna acts as a spoiler, the polarity of the secondary antenna is opposite that of the first antenna. In the embodiment in which the secondary antenna acts in booster mode, the polarities of the two antennae share the same direction. The latter mode of operation of the invention is generally equivalent to an axially-symmetric central NMR logging tool and is most fit for operation in a small borehole region. In the former mode of operation, wherein the secondary antenna operates in a spoiler mode, the device becomes equivalent to a side-looking NMR device, and is suitable for large boreholes in which the logging tool will be placed against the borehole walls.

In both modes of operation, the primary antenna is intended to operate during both the transmission and receiving portions of the mode. Furthermore, when the secondary antenna operates in a spoiler mode, the secondary antenna optionally operates only during the transmission portions of the excitation pulse sequence, and then is turned off during the receiving portion of the sequence. When operated, during the transmission portion of this mode, the magnetic field lines are prominent within the rock formation being considered. Since the primary antenna is placed up against the borehole wall, correspondingly magnetic field lines are reduced in strength in the volume inside the borehole. During the receiving portion, the secondary antenna may be turned off so as not to receive spurious signals from the borehole cavity, which is situated at the back side of the magnetic assembly.

When the secondary antenna operates in booster mode, however, it operates during both the transmission and receiving portions of the pulse sequence. Operating during the transmission portion realizes a RF magnetic field line from the back side of the tool, which is contained generally within the surrounding rock formation. It is then desirable to operate the secondary antenna as a receiver in the receiving portion of the CPMG pulse.

Figure 2:
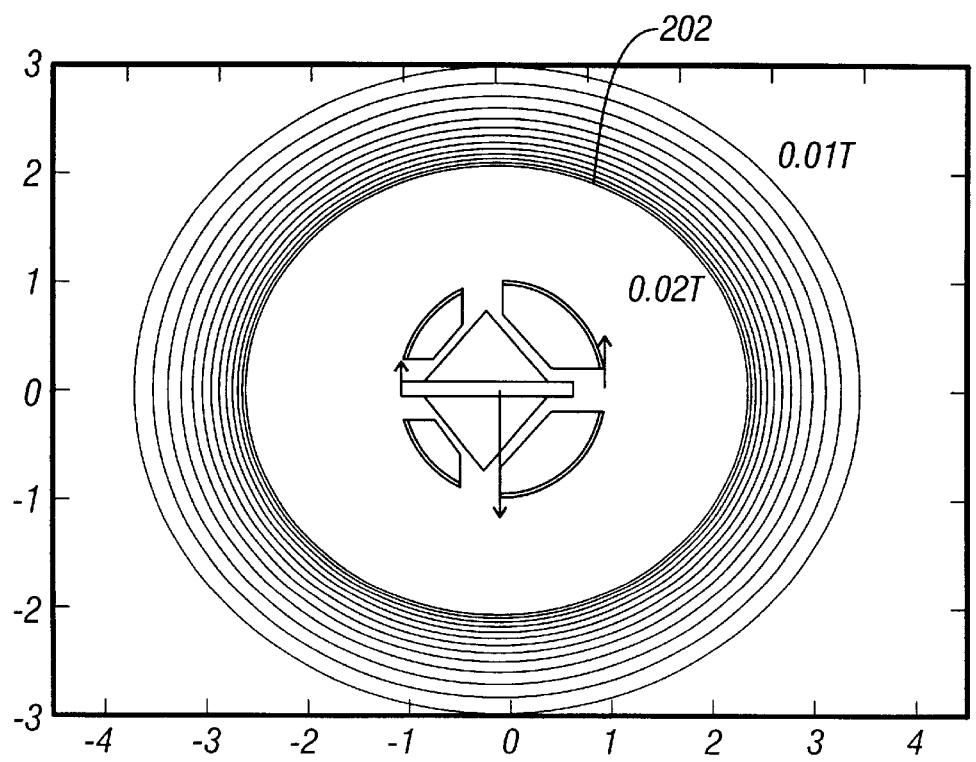
FIG. 2 shows the iso-lines of the static magnetic field surrounding the NMR logging tool.

FIG. 2 shows the magnetic assembly of FIG. 1 with iso-lines of the static magnetic field of the permanent magnet surrounding the NMR logging tool. Magnetic strength decreases with distance from the magnet, as expected. The NMR conditions are to be met near one of the iso-lines shown. An iso-line is selected by changing the frequency of the RF excitation field.

Figure 3:
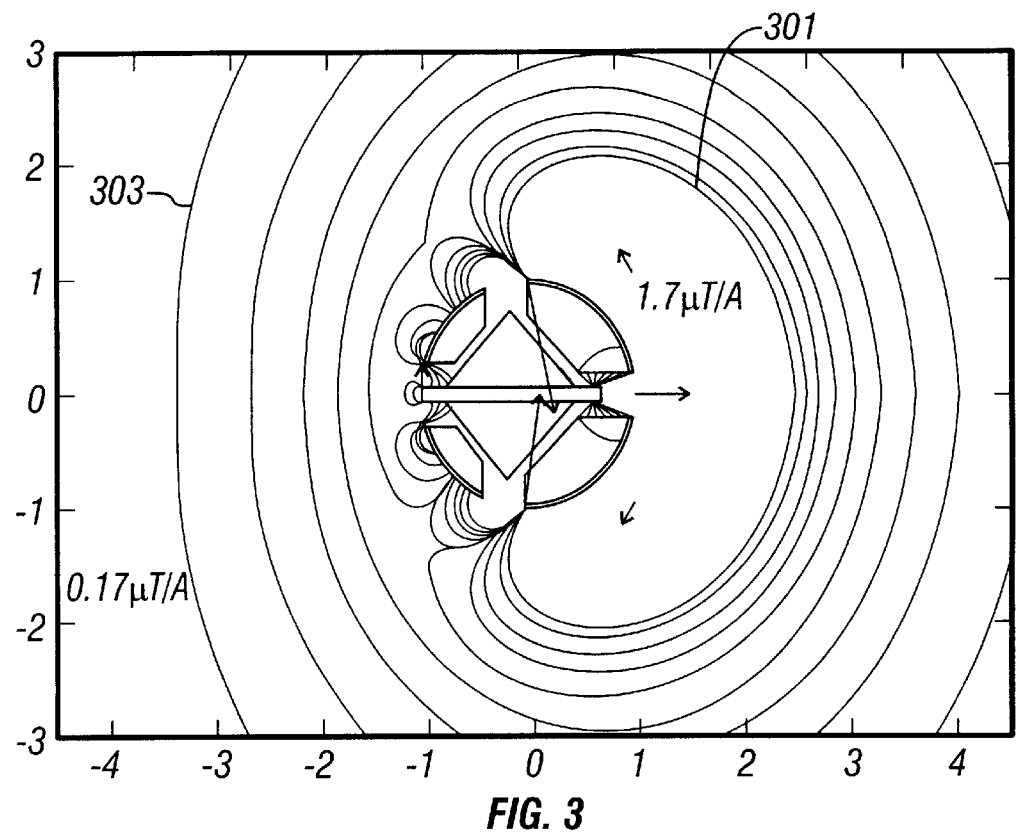
FIG. 3 shows the iso-lines of relative coupling of the RF antenna of the NMR device while in the receiving portion of a side-looking mode.
Figure 4:
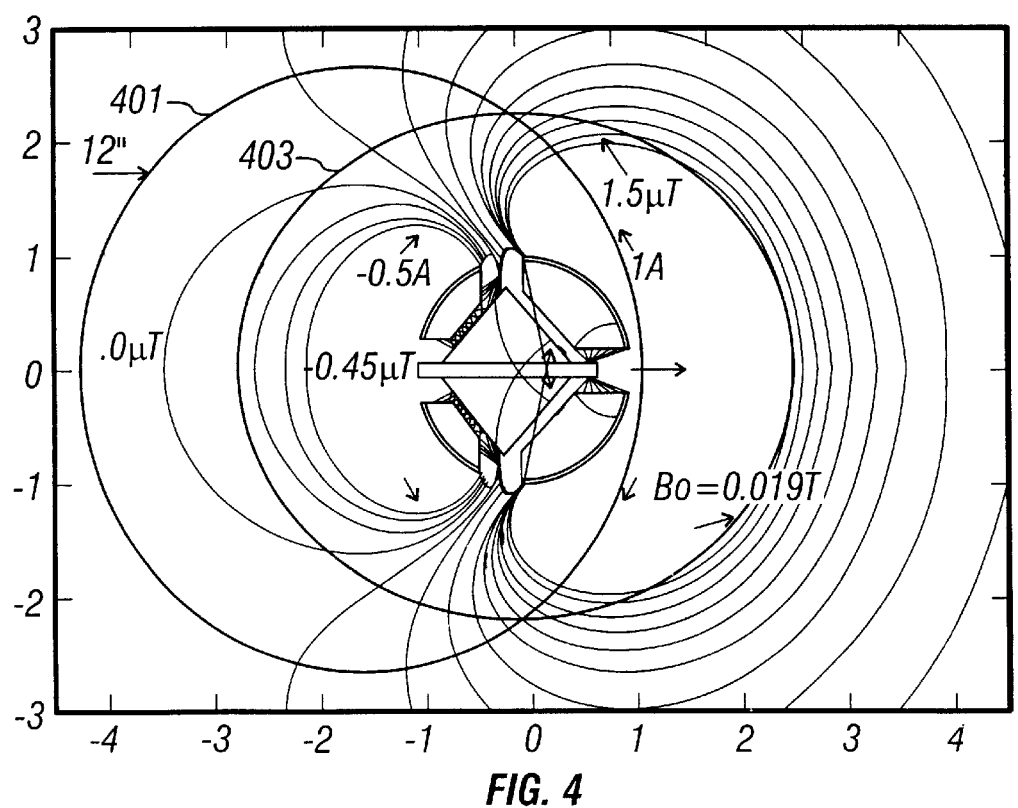
FIG. 4 shows the effective RF field generated by the two antennae while in the transmitting portion of a side-looking mode.

FIGS. 3 and 4 present the "side-looking" operation mode optimized for large boreholes in the receiving and transmitting portions of the mode respectively. FIG. 3 shows the iso-lines of relative coupling of the RF antenna in the sensitive volume, during the portion in which NMR signals are received. In FIG. 3, the second antenna does not contribute to the signal. It is evident from FIG. 3 that signals at the front side of the device are significantly greater than signals at the back side. As an example, the isoline near the front side 301 has a signal strength of 1.7 $\mu$T/A, whereas a signal from the back 302 has a strength of 0.17 $\mu$T/A.

FIG. 4 presents an example of the invention working in a side-looking mode inside of a borehole 401 whose diameter is chosen as 12" for the purpose of illustration. A static magnetic field iso-line, labeled $B_0$=0.019T, 402 is also presented to illustrate that a portion of the potential excitation volume lies within the borehole 401. Also shown is the effective RF field generated by the two antennae operating in the transmission portion of the pulse sequence. The current in the second antenna opposes the current in the first antenna and has a magnitude generally of 50% of the magnitude of the current in the first antenna. As an example, in FIG. 4, antenna 1 carries a current of 1A, while the antenna 2 carries a current of −0.5A. This configuration of currents reduces the magnetic field in the borehole region, preventing conditions under which NMR excitation can occur in the borehole.

In the side-looking mode of operation, the second antenna may be switched off during the receive period. Optionally, the second antenna may be used as an indicator of the residual signal from the borehole. The error signal could be estimated and corrected for by software means. It can be seen in FIG. 4 that the effective RF field and the static magnetic fields match each other approximately on the 120° arc. This arc of match defines the sensitivity region in the case of the "side-looking" operation mode. Whereas a magnetic field of 1.5μT is formed on the front side of the device, a magnetic field of negligible strength is found on the back side.

Figure 5:
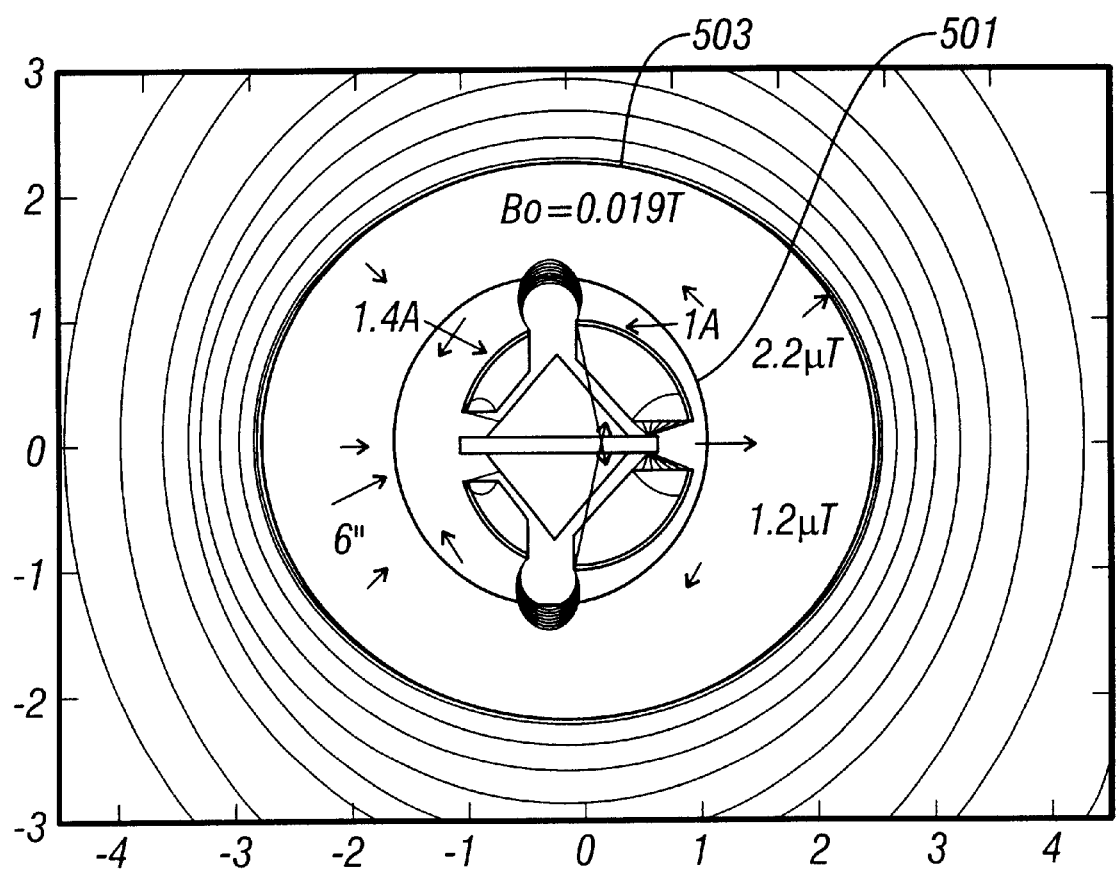
FIG. 5 shows the RF field iso-lines of the device used in the central mode.

FIG. 5 presents the NMR logging tool operation mode optimized for small boreholes. The borehole in FIG. 5 is labeled 501. Typical small boreholes are of diameter equal to or less than 8". FIG. 5 also shows the static magnetic field iso-line 502, which defines the shape of the sensitivity region. The field is reduced compared to the "side-looking" mode in order to ensure a required minimum penetration into the formation. When in the transmitting portion, the second antenna generates a RF magnetic field additive to the first antenna field so the total effective RF field matches the static magnetic field generally at all points around the logging tool. In this case, the current in the second antenna circulates in the same direction as the current in the first antenna. Its current intensity is about 1.4 times the current intensity of the first antenna. Both first antenna and second antenna contribute to the received signal in this case. In accordance with the reciprocity theorem, the amplitude of the received signal in the second antenna will be 40% less than that of the first antenna. When adding up received signals of the two antennas, the weighting factor may be used, for example, in order to optimize the SNR.

The central mode of operation will provide a clearer signal than the side-looking mode, due to an improvement of the signal-to-noise ratio. The effectiveness of using the central-like mode of operation is illustrated in the following example of SNR calculation. Assume that a constant azimuthal sensitivity of the logging tool is desired. Then the voltage across the second antenna should be amplified 1.4 times. This means that for equally noisy antennas with noise voltage $N_a$, the resultant noise would be $N_a$. The following expression can be used to estimate the NMR signal in the assumption of unchanged excitation frequency and the bandwidth $$S \propto \frac{B_a}{I_a} \cdot \alpha_{\text{arc}}$$

In the expression above, the ratio $B_a/I_a$ represents the coupling of the antenna with the sensitive region, and $\alpha_{\text{arc}}$ is the angle of the sensitivity arc. It is clear from examining magnetic field values in FIGS. 3–5 that the arc angle in the "side-looking" mode is approximately one-third the value of the arc angle in the "central" mode. Also, the coupling in the "side-looking" mode is less by a factor of 1.3 the value of the coupling in the "central" mode. Thus, in this case, the expected increase in the SNR for the central mode is about 2.5 times. This example corresponds to the case of about 6" borehole. For larger borehole diameter the central-like mode will require that the excitation frequency be reduced compared to side-looking mode. This will reduce the SNR improvement factor and eventually make the central mode ineffective.

The tool described above is preferably used by pulsing the primary antenna with a CPMG sequence or a modified CPMG sequence such as that described by Reiderman (U.S. Pat. No. 6,163,153). When the secondary antenna is used in the boost mode in a small diameter borehole, it too is pulsed with the same sequence as is the primary antenna.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A Nuclear Magnetic Resonance (NMR) apparatus comprising:
   (a) a permanent magnet assembly for producing a static magnetic field in a region of examination;
   (b) a primary antenna for generating a first RF magnetic field in a region of examination, said first RF field having a direction substantially perpendicular to a direction of the static field in said region;
   (c) a secondary antenna generating a second PF magnetic field having a direction substantially perpendicular to the static field in said region, said secondary antenna adaptable to operate in a mode selected from the group consisting of (i) a spoiler mode wherein said second RF field has a substantial component anti-parallel to said first RF field in a specified region, and, (ii) a booster mode wherein said second RF field has a substantial component parallel to said first RF field in a specified region;
   wherein said spoiler mode is used when the apparatus is used in a large borehole and said booster mode is used when the apparatus is used in a small borehole.

2. The NMR apparatus of claim 1, wherein the magnet assembly further comprises: at least two spaced apart magnets, having a magnetization direction substantially perpendicular to an axis of the NMR apparatus.

3. The NMR apparatus of claim 1 wherein the RF field direction of the primary antenna is oriented substantially perpendicular to an axis of the NMR apparatus.

4. The NMR apparatus of claim 1 wherein the primary antenna further comprises a first antenna winding and a first soft magnetic core, said first winding and first core being positioned to a first side of the permanent magnet.

5. The NMR apparatus of claim 1 wherein the RF field direction of the secondary antenna is oriented substantially perpendicular to the axis of the NMR apparatus.

6. The NMR apparatus of claim 4 wherein the secondary antenna further comprises a second antenna winding and a second soft magnetic core, said second winding and second core being positioned to a second side of the permanent magnet opposite the first side.

7. A method of NMR well logging comprising:
   (a) conveying a logging tool into a wellbore;
   (b) using a permanent magnet on the logging tool for inducing a static magnetic field in a region of examination;

(c) using a primary antenna on a first side of the permanent magnet on the logging tool for inducing a first RF field in the region of examination, said first RF field having a direction substantially perpendicular to a direction of the static magnetic field in the region of examination;

(d) using a secondary antenna on a second side of the permanent magnet opposite the first side of the permanent magnet or inducing a second RF field, the second RP field having a field direction that is selected from (i) having a substantial component parallel to the first RF field in a specified region when said logging tools is used in a small diameter wellbore, and, (ii) having a substantial component anti-parallel to the first RF field in a specified region when said logging tool is used in a large diameter wellbore;

(e) pulsing the primary and secondary antennae with a pulsed RF field to produce spin-echo signals from nuclei in the region of examination; and (f) using at least the primary antenna to receive said spin-echo signals.

8. The method of claim 7 wherein the pulsed RF magnetic field comprises an excitation pulse and a plurality of refocusing pulses.

9. The method of claim 7 wherein the second RF field is substantially parallel to the first RF field in the specified region, and wherein the combination of the first and second RF field produces a resultant RF magnetic field generally matching an iso-line of the static magnetic field on substantially all sides of the logging tool.

10. The method of claim 7 wherein the second RF field is substantially parallel to the first RF field in said specified region, the method further comprising using the secondary antenna to receive said spin-echo signals.

11. The method of claim 7 wherein the second RF field is substantially anti-parallel to the first RF field in said specified region, and wherein the combination of the first and second magnetic fields produces a resultant RF magnetic field that is generally matching an iso-line of the static magnetic field on the first side and that is generally reduced to zero on the second side.

12. The method of claim 7 wherein when the second RF field is substantially anti-parallel to the first RF field in said specified region, the method further comprising using the secondary antenna for receiving the spin-echo signals and using said signals received by the secondary antes as an indication of signals from a fluid within the wellbore.

13. The method of claim 9, wherein the region of examination lies substantially within a rock formation surrounding the wellbore and wherein a diameter of said wellbore is slightly greater than a diameter of the apparatus, the method further comprising positioning the logging tool substantially concentrically within said wellbore.

14. The method of claim 11, wherein the region of examination lies substantially within a rock formation surrounding the wellbore and wherein a diameter of said borehole is substantially greater than a diameter of the logging tool, the method further comprising positioning the logging tool eccentrically within said wellbore.

15. The NMR apparatus of claim 1 wherein said specified region comprises a portion of the borehole.

16. The method of claim 7 wherein said specified region comprises a portion of the borehole.

* * * * *